United States Patent [19]

Kung et al.

[11] Patent Number: 4,654,210
[45] Date of Patent: Mar. 31, 1987

[54] METHODS AND COMPOSITIONS USING COMPLEMENT FIXING MONOCLONAL ANTIBODY TO HUMAN T CELLS

[75] Inventors: Patrick C. Kung, Bridgewater; Gideon Goldstein, Short Hills, both of N.J.

[73] Assignee: Ortho Pharmaceutical Corporation, Raritan, N.J.

[21] Appl. No.: 709,232

[22] Filed: Mar. 6, 1985

Related U.S. Application Data

[62] Division of Ser. No. 432,452, Oct. 4, 1982, Pat. No. 4,515,893, which is a division of Ser. No. 33,669, Apr. 26, 1979, Pat. No. 4,361,549.

[51] Int. Cl.$^4$ .................... A61K 39/395; C12N 15/00; G01N 33/53
[52] U.S. Cl. ........................................ 424/85; 436/548; 435/172.2
[58] Field of Search ...................... 435/172.2, 240, 543; 424/85; 260/112 R, 112 B; 436/548

[56] References Cited

U.S. PATENT DOCUMENTS 4,172,124 10/1979 Koprowski ............................ 424/85
4,196,265  4/1980 Koprowski ............................ 424/85
4,284,412  8/1981 Hansen ................................. 23/230 B Primary Examiner—Blondel Hazel
Attorney, Agent, or Firm—Geoffrey G. Dellenbaugh

[57] ABSTRACT

Hybrid cell line for production of monoclonal antibody to an antigen found on all normal human T cells and cutaneous T lymphoma cells. The hybrid is formed by fusing splenocytes from immunized $CAF_1$ mice with P3X63Ag8U1 myeloma cells. Diagnostic and therapeutic uses of the monoclonal antibody are also disclosed.

15 Claims, 5 Drawing Figures

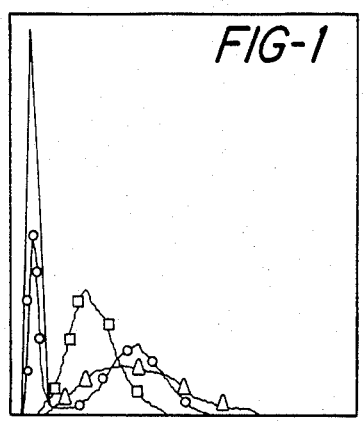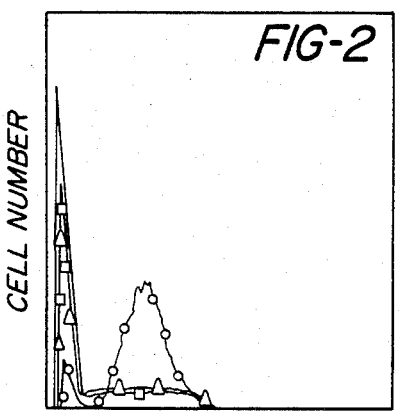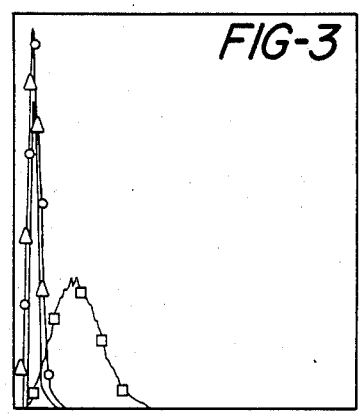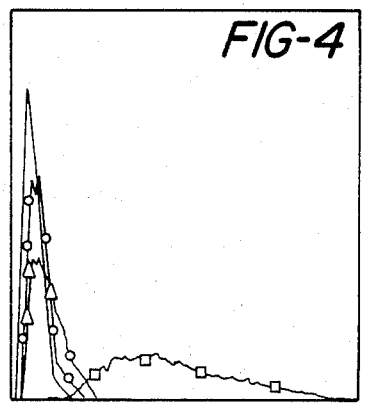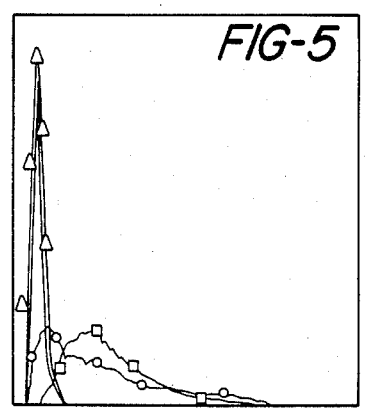

METHODS AND COMPOSITIONS USING COMPLEMENT FIXING MONOCLONAL ANTIBODY TO HUMAN T CELLS

This application is a division of our copending application Ser. No. 432,452, filed Oct. 4, 1982, now U.S. Pat. No. 4,515,893, which in turn is a division of application Ser. No. 33,669, filed Apr. 26, 1979, now U.S. Pat. No. 4,361,549.

FIELD OF THE INVENTION

This invention relates generally to new hybrid cell lines and more specifically to hybrid cell lines for production of complement-fixing monoclonal antibody to an antigen found on all normal human T cells and cutaneous T lymphoma cells, to the antibody so produced, and to therapeutic and diagnostic methods and compositions employing this antibody.

DESCRIPTION OF THE PRIOR ART

The fusion of mouse myeloma cells to spleen cells from immunized mice by Kohler and Milstein in 1975 [*Nature* 256, 495–497 (1975)] demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations. See, for example, *Current Topics in Microbiology and Immunology*, Volume 81—"Lymphocyte Hybridomas", F. Melchers, M. Potter, and N. Warner, Editors, Springer-Verlag, 1978, and references contained therein; C. J. Barnstable, et al., *Cell*, 14, 9–20 (May, 1978); P. Parham and W. F. Bodmer, *Nature* 276, 397-399 (November, 1978); *Handbook of Experimental Immunology*, Third Edition, Volume 2, D. M. Wier, Editor, Blackwell, 1978, Chapter 25; and *Chemical and Engineering News*, Jan. 1, 1979, 15–17 the subject hybridoma was deposited with the American Type Culture Collection, 12301 Parklawn Drive, Rockville, Mar., 20852 on Apr. 26, 1979, and assigned the ATCC accession number CRL 8001. These references simultaneously indicate the rewards and complications of attempting to produce monoclonal antibody from hybridomas. While the general technique is well understood conceptually, there are many difficulties met and variations required for each specific case. In fact, there is no assurance, prior to attempting to prepare a given hybridoma, that the desired hybridoma will be obtained, that it will produce antibody if obtained, or that the antibody so produced will have the desired specificity. The degree of success is influenced principally by the type of antigen employed and the selection technique used for isolating the desired hybridoma.

The attempted production of monoclonal antibody to human lymphocyte cell-surface antigens has been reported only in a few instances. See, for example, *Current Topics in Microbiology and Immunology*, ibid, 66–69 and 164–169. The antigens used in these reported experiments were cultured human lymphoblastoid leukemia and human chronic lymphocytic leukemia cell lines. Many hybridomas obtained appeared to produce antibody to various antigens on all human cells. None of the hybridomas produced antibody against a predefined class of human lymphocytes.

It should be understood that there are two principal classes of lymphocytes involved in the immune system of humans and animals. The first of these (the thymus-derived cell or T cell) is differentiated in the thymus from haemopoietic stem cells. While within the thymus, the differentiating cells are termed "thymocytes." The mature T cells emerge from the thymus and circulate between the tissues, lymphatics, and the bloodstream. These T cells form a large proportion of the pool of recirculating small lymphocytes. They have immunological specificity and are directly involved in cell-mediated immune responses (such as graft rejection) as effector cells. Although T cells do not secrete humoral antibodies, they are sometimes required for the secretion of these antibodies by the second class of lymphocytes discussed below. Some types of T cells play a regulating function in other aspects of the immune system. The mechanism of this process of cell cooperation is not yet completely understood.

The second class of lymphocytes (the bone marrow-derived cells or B cells) are those which secrete antibody. They also develop from haemopoietic stem cells, but their differentiation is not determined by the thymus. In birds, they are differentiated in an organ analogous to the thymus, called the Bursa of Fabricius. In mammals, however, no equivalent organ has been discovered, and it is thought that these B cells differentiate within the bone marrow.

It is now recognized that T cells are divided into at least several subtypes, termed "helper", "suppressor", and "killer" T cells, which have the function of (respectively) promoting a reaction, suppressing a reaction, or killing (lysing) foreign cells. These subclasses are well understood for murine systems, but they have only recently been described for human systems. See, for example, R. L. Evans, et al., *Journal of Experimental Medicine*, Volume 145, 221–232, 1977; and L. Chess and S. F. Schlossman—"Functional Analysis of Distinct Human T-Cell Subsets Bearing Unique Differentiation Antigens", in "*Contemporary Topics in Immunobiology*", O. Stutman, Editor, Plenum Press, 1977, Volume 7, 363–379.

The ability to identify or suppress classes or subclasses of T cells is important for diagnosis or treatment of various immunoregulatory disorders or conditions.

For example, certain leukemias and lymphomas have differing prognosis depending on whether they are of B cell or T cell origin. Thus, evaluation of the disease prognosis depends upon distinguishing between these two classes of lymphocytes. See, for example, A. C. Aisenberg and J. C. Long, *The American Journal of Medicine*, 58:300 (March, 1975); D. Belpomme, et al., in "*Immunological Diagnosis of Leukemias and Lymphomas*", S. Thierfelder, et al., eds, Springer, Heidelberg, 1977, 33–45; and D. Belpomme, et al., *British Journal of Haematology*, 1978, 38, 85. Certain disease states (e.g., juvenile rheumatoid arthritis and certain leukemias) are associated with an imbalance of T cell subclasses. It has been suggested that autoimmune diseases generally are associated with an excess of "helper" T cells or a deficiency of certain "suppressor" T cells, while malignancies generally are associated with an excess of "suppressor" T cells. In certain leukemias, excess T cells are produced in an arrested stage of development. Diagnosis may thus depend on the ability to detect this imbalance or excess. See, for example, J. Kersey, et al., "Surface Markers Define Human Lymphoid Malignancies with Differing Prognoses" in *Ha-*

*ematology and Blood Transfusion,* Volume 20, Springer-Verlag, 1977, 17-24, and references contained therein.

On the therapeutic side, there is some suggestion, as yet not definitely proven, that administration of antibodies against the subtype of T cell in excess may have therapeutic benefit in autoimmune disease or malignancies. Antisera against the entire class of human T cells (so-called antihuman thymocyte globulin or ATG) has been reported useful therapeutically in patients receiving organ transplants. Since the cell-mediated immune response (the mechanism whereby transplants are rejected) depends upon T cells, administration of antibody to T cells prevents or retards this rejection process. See, for example, Cosimi, et al., "Randomized Clinical Trial of ATG in Cadaver Renal Allgraft Recipients: Importance of T Cell Monitoring", *Surgery* 40:155-163 (1976) and references contained therein.

The identification and suppression of human T cell classes and subclasses has previously been accomplished by the use of spontaneous autoantibodies or selective antisera for human T cells obtained by immunizing animals with human T cells, bleeding the animals to obtain serum, and adsorbing the antiserum with (for example) autologous but not allogeneic B cells to remove antibodies with unwanted reactivities. The preparation of these antisera is extremely difficult, particularly in the adsorption and purification steps. Even the adsorbed and purified antisera contain many impurities in addition to the desired antibody, for several reasons. First, the serum contains millions of antibody molecules even before the T cell immunization. Second, the immunization causes production of antibodies against a variety of antigens found on all human T cells injected. There is no selective production of antibody against a single antigen. Third, the titer of specific antibody obtained by such methods is usually quite low, (e.g., inactive at dilutions greater than 1:100) and the ratio of specific to non-specific antibody is less than $1/10^6$.

See, for example, the Chess and Schlossman article referred to above (at pages 365 and following) and the Chemical and Engineering News article referred to above, where the deficiencies of prior art antisera and the advantages of monoclonal antibody are described.

SUMMARY OF THE INVENTION

There has now been discovered a novel hybridoma (designated OKT3) which is capable of producing novel complementfixing monoclonal antibody against an antigen found on essentially all normal human peripheral T cells and cutaneous T lymphoma cells. The antibody so produced is mono-specific for a single determinant on normal human T cells and cutaneous T lymphoma cells and contains essentially no other antihuman immuneglobulin, in contrast to prior art antisera (which are inherently contaminated with antibody reactive to numerous human antigens) and to prior art monoclonal antibodies (which are not monospecific for a human T cell antigen). Moreoever, this hybridoma can be cultured to produce antibody without the necessity of immunizing and killing animals, followed by the tedious adsorption and purification steps necessary to obtain even the impure antisera of the prior art.

It is accordingly one object of this invention to provide hybridomas which produce antibodies against an antigen found on essentially all normal human T cells and cutaneous T lymphoma cells.

It is a further aspect of the present invention to provide methods for preparing these hybridomas.

A further object of the invention is to provide essentially homogeneous antibody against an antigen found on essentially all normal human T cells and cutaneous T lymphoma cells.

A still further object is to provide methods for treatment or diagnosis of disease employing these antibodies.

Other objects and advantages of the invention will become apparent from the examination of the present disclosure.

In satisfaction of the foregoing objects and advantages, there is provided by this invention a novel hybridoma producing novel antibody to an antigen found on essentially all normal human T cells and cutaneous T lymphoma cells, the antibody itself, and diagnostic and therapeutic methods employing the antibody. The hybridoma was prepared generally following the method of Milstein and Kohler. Following immunization of mice with normal E rosette positive human T cells, the spleen cells of the immunized mice were fused with cells from a mouse myeloma line and the resultant hybridomas screened for those with supernatants containing antibody which gave selective binding to normal E rosette positive human T cells. The desired hybridomas were subsequently cloned and characterized. As a result, a hybridoma was obtained which produces antibody (designated OKT3) against an antigen on essentially all normal human T cells. Not only does this antibody react with essentially all normal human peripheral T cells, but it also does not react with other normal peripheral blood lymphoid cells. In addition, the cell surface antigen recognized by this antibody is detected on only mature thymocytes and is completely lacking on greater than 90% of normal human thymocytes.

In view of the difficulties indicated in the prior art and the lack of success reported using malignant cell lines as the antigen, it was surprising that the present method provided the desired hybridoma. It should be emphasized that the unpredictable nature of hybrid cell preparation does not allow one to extrapolate from one antigen or cell system to another. In fact, the present applicants have discovered that using a T cell malignant cell line as the antigen caused formation of hybridomas which did not produce the desired antibody. Attempts to use purified antigens separated from the cell surfaces were also unsuccessful.

Both the subject hybridoma and the antibody produced thereby are identified herein by the designation "OKT3", the particular material referred to being apparent from the context.

The preparation and characterization of the hybridoma and the resultant antibody will be better understood by reference to the following description and Examples.

DETAILED DESCRIPTION OF THE INVENTION

The method of preparing the hybridoma generally comprises the following steps:

A. Immunizing mice with E rosette positive purified normal human peripheral T cells. While it has been found that female $CAF_1$ mice (a first generation hybrid between Balb/cJ and A/J mice) are preferred, it is contemplated that other mouse strains could be used. The immunization schedule and T cell concentration should be such as to produce useful quantities of suitably primed splenocytes. Three immunizations at fourteen day intervals with $2 \times 10^7$ cells/mouse/injection in 0.2 ml phosphate buffered saline has been found to be effective.

B. Removing the spleens from the immunized mice and making a spleen suspension in an appropriate medium. About one ml of medium per spleen is sufficient. These experimental techniques are well-known.

C. Fusing the suspended spleen cells with mouse myeloma cells from a suitable cell line by the use of a suitable fusion promoter. The preferred ratio is about 5 spleen cells per myeloma cell. A total volume of about 0.5-1.0 ml of fusion medium is appropriate for about $10^8$ splenocytes. Many mouse myeloma cell lines are known and available, generally from members of the academic community or various deposit banks, such as the Salk Institute Cell Distribution Center, La Jolla, CA. The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine guanine phophoribosyl transferase and hence will not be supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred. While the preferred fusion promoter is polyethylene glycol having an average molecular weight from about 1000 to about 4000 (commercially available as PEG 1000, etc.), other fusion promoters known in the art may be employed.

D. Diluting and culturing in separate containers, the mixture of unfused spleen cells, unfused myeloma cells, and fused cells in a selective medium which will not support the unfused myeloma cells for a time sufficient to allow death of the unfused cells (about one week). The dilution may be a type of limiting one, in which the volume of diluent is statistically calculated to isolate a certain number of cells (e.g., 1-4) in each separate container (e.g., each well of a microtiter plate). The medium is one (e.g., HAT medium) which will not support the drug-resistant (e.g., 8-azaguanine resistant) unfused myeloma cell line. Hence, these myeloma cells perish. Since the unfused spleen cells are non-malignant, they have only a finite number of generations. Thus, after a certain period of time (about one week) these unfused spleen cells fail to reproduce. The fused cells, on the other hand, continue to reproduce because they possess the malignant quality of the myeloma parent and the ability to survive in the selective medium of the spleen cell parent.

E. Evaluating the supernatant in each container (well) containing a hybridoma for the presence of antibody to E rosette positive purified human T cells.

F. Selecting (e.g., by limiting dilution) and cloning hybridomas producing the desired antibody.

Once the desired hybridoma has been selected and cloned, the resultant antibody may be produced in one of two ways. The purest monoclonal antibody is produced by in vitro culturing of the desired hybridoma in a suitable medium for a suitable length of time, followed by recovery of the desired antibody from the supernatant. The suitable medium and suitable length of culturing time are known or are readily determined. This in vitro technique produces essentially monospecific monoclonal antibody, essentially free from other specific antihuman immune globulin. There is a small amount of other immune globulin present since the medium contains xenogeneic serum (e.g., fetal calf serum). However, this in vitro method may not produce a sufficient quantity or concentration of antibody for some purposes, since the concentration of monoclonal antibody is only about 50 μg/ml.

To produce a much greater concentration of slightly less pure monoclonal antibody, the desired hybridoma may be injected into mice, preferably syngenic or semi-syngenic mice. The hybridoma will cause formation of antibody-producing tumors after a suitable incubation time, which will result in a high concentration of the desired antibody (about 5-20 mg/ml) in the bloodstream and peritoneal exudate (ascites) of the host mouse. Although these host mice also have normal antibodies in their blood and ascites, the concentration of these normal antibodies is only about 5% of the monoclonal antibody concentration. Moreover, since these normal antibodies are not antihuman in their specificity, the monoclonal antibody obtained from the harvested ascites or from the serum is essentially free of any contaminating antihuman immune globulin. This monoclonal antibody is high titer (active at dilutions of 1:100,000 or higher) and high ratio of specific to non-specific immune globulin (about 1/20). Immune globulin produced incorporating the κ light myeloma chains are non-specific, "nonsense" peptides which merely dilute the monoclonal antibody without detracting from its specificity.

EXAMPLE I

Production of Monoclonal Antibodies

A. Immunization and Somatic Cell Hybridization

Female $CAF_1$ mice (Jackson Laboratories; 6–8 weeks old) were immunized intraperitoneally with $2 \times 10^7$ E rosette purified T cells in 0.2 ml of phosphate buffered saline at 14-day intervals. Four days after the third immunization, spleens were removed from the mice, and a single cell suspension was made by pressing the tissue through a stainless steel mesh.

Cell fusion was carried out according to the procedure developed by Kohler and Milstein. $1 \times 10^8$ splenocytes were fused in 0.5 ml of a fusion medium comprising 35% polyethylene glycol (PEG 1000) and 5% dimethylsulfoxide in RPMI 1640 medium (Gibco, Grand Island, NY) with $2 \times 10^7$ P3X63Ag8U1 myeloma cells supplied by Dr. M. Scharff, Albert Einstein College of Medicine, Bronx, NY. These myeloma cells secrete $IgG_1$ κ light chains.

B. Selection and Growth of Hybridoma

After cell fusion, cells were cultured in HAT medium (hypoxanthine, aminopterin, and thymidine) at 37° C. with 5% $CO_2$ in a humid atmosphere. Several weeks later, 40 to 100 μl of supernatant from cultures containing hybridomas were added to a pellet of $10^6$ peripheral lymphocytes separated into E rosette positive [E ) and E rosette negative (E−) populations, which were prepared from blood of healthy human donors as described by Mendes (J. *Immunol.* 111:860, 1973). Detection of mouse hybridoma antibodies binding to these cells was determined by radioimmunoassay and/or indirect immunofluorescence. In the first method, the cells were initially reacted with 100 μl of affinity-purified $^{125}I$ goat-anti-mouse IgG ($10^6$ cpm/μg; 500 μg/μl). (Details of iodination of goat-anti-mouse IoG were described by Kung, et al., *J. Biol. Chem.* 251(8):2399, 1976). Alternatively, cells incubated with culture supernatants were stained with a fluorescinated goat-anti-mouse IgG (G/M FITC) (Meloy Laboratories, Springfield, VA; F/p =2.5) and the fluorescent antibody-coated cells were subsequently analyzed on the Cytofluorograf FC200/4800A (Ortho Instruments, Westwood, MA) as described in Example III. Hybridoma cultures containing antibodies reacting specifically with E+ lymphocytes (T cells) were selected and cloned. Subsequently, the clones were transferred intraperitoneally by injecting $1 \times 10^7$ cells of a given clone (0.2 ml volume) into CAF$_1$ mice primed with 2,6,10,14-tetramethylpentadecane, sold by Aldrich Chemical Company under the name Pristine. The malignant ascites from these mice were then used to characterize lymphocytes as described below in Example II. The subject hybrid antibody OKT3 was demonstrated by standard techniques to be of IgG$_2$ subclass and to fix complement.

EXAMPLE II

Characterization of OKT3 Reactivity

A. Isolation of Lymphocyte Populations

Human peripheral blood mononuclear cells were isolated from healthy volunteer donors (ages 15-40) by FicollHypaque density gradient centrifugation (Pharmacia Fine Chemicals, Piscataway, NJ) following the technique of Boyum, *Scand. J. Clin. Lab. Invest.* 21 (Suppl. 97): 77, 1968. Unfractionated mononuclear cells were separated into surface Ig+ (B) and Ig− (T plus Null) populations by Sephadex G-200 anti-F(ab')$_2$ column chromatography as previously described by Chess, et al., *J. Immunol.* 113:1113 (1974). T cells were recovered by E rosetting the Ig− population with 5% sheep erythrocytes (Microbiological Associates, Bethesda, MD). The rosetted mixture was layered over Ficoll-Hypaque and the recovered E+ pellet treated with 0.155M NH$_4$Cl ($10^8$ ml per cells). The T cell population so obtained was <2% EAC rosette positive and >95% E rosette positive as determined by standard methods. In addition, the non-rosetting Ig− (Null cell) population was harvested from the Ficoll interface. This latter population was <5% E+ and ≦2% sIg+. The surface Ig+ (B) population was obtained from the Sephadex G-200 column following elution with normal human gamma globulin as previously described. This population was >95% surface Ig+ and <5% E+.

Normal human macrophages were obtained from the mononuclear population by adherence to polystyrene. Thus, mononuclear cells were resuspended in final culture media (RPMI 1640, 2.5 mM HEPES [4-(2-hydroxyethyl)-1-piperazinepropane sulfonic acid]buffer, 0.5% sodium bicarbonate, 200 mM L-glutamine, and 1% penicillinstreptomycin, supplemented with 20% heat-inactivated human AB serum) at a concentration of $2 \times 10^6$ cells and incubated in plastic petri dishes (100×20 mm) (Falcon Tissue Culture Dish; Falcon, Oxnard, CA) at 37° C. overnight. After extensive washing to remove non-adherent cells, the adherent population was detached by brisk washing with cold serum-free medium containing 2.5 mM EDTA and occasional scraping with the rubber tip of a disposable syringe plunger. Greater than 85% of the cell population was capable of ingesting latex particles and had morphologic characteristics of monocytes by Wright-Giemsa staining.

B. Normal Thymus

Normal human thymus gland was obtained from patients aged two months to 14 years undergoing corrective cardiac surgery. Freshly obtained portions of the thymus gland were immediately placed in 5% fetal calf serum in medium 199 (Gibco), finely minced with forceps and scissors, and subsequently made into single cell suspensions by being pressed through wire mesh. The cells were next layered over Ficoll-Hypaque and spun and washed as previously described in section A above. The thymocytes so obtained were >95% viable and ≧90% E rosette positive.

C. Cell Lines

Epstein-Barr Virus (EBV) transformed B cell lines from four normal individuals (Iaz 007, Laz 156, Laz 256, and SB) and described. T cell lines CEM, HJD-1, Laz 191, and HM1 established from leukemic patients were provided by Dr. H. Lazarus, Sidney Farber Cancer Institute, Boston, MA.

D. .T Acute Lymphoblastic Leukemia (T-ALL) Cells and T Chronic Lymphatic Leukemia (T-CLL) Cells Leukemia cells were obtained from 12 patients with T-ALL. These individuals' cells had previously been determined to be of T cell lineage by their spontaneous rosette formation with sheep erythrocytes (>20% E+) reactivity with T cell specific hetero-antisera, antiHTL (anti-B.K.) and A99, as previously described by Schlossman, et al., *Proc. Nat. Acad. Sci.* 73:1288 (1976). Tumor cells from three individuals were reactive (TH$_2$+) with rabbit and/or equine anti-TH$_2$ while cells from the remaining nine were non-reactive (TH$_2$) Leukemic cells from two patients with TH$_2$− T-CLL were also utilized. Both acute and chronic T cell leukemia cells were cryopreserved in −196° C. vapor phase liquid nitrogen in 10% dimethylsulfoxide and 20% AB human serum until the time of surface characterization. The tumor populations analyzed were >90% blasts by Wright-Giemsa morphology in all instances.

EXAMPLE III

Cytofluorographic Analysis

Cytofluorographic analysis of all cell populations was performed by indirect immunofluorescence with fluorescein-conjugated goat-anti-mouse IgG (G/M FITC) (Meloy Laboratories) on a Cytofluorograf FC200/4800A (Ortho Instruments). In brief, $1-2 \times 10^6$ cells were treated with 0.15 ml OKT3 at a 1:1000 dilution, incubated at 4° C. for 30 minutes, and washed twice. The cells were then reacted with 0.15 ml of a 1:40 dilution G/M FITC at 4° C. for 30 minutes, centrifuged, and washed three times. These cells were then analyzed on the Cytofluorograf and the intensity of fluorescence per cell recorded on a pulse height analyzer. A similar pattern of reactivity was observed at a dilution of 1:100,000, but further dilution caused loss of reactivity. Background staining was obtained by substituting a 0.15 ml aliquot of 1:1000 ascites from a Balb/cJ mouse intraperitoneally immunized with a non-producing hybrid clone.

BRIEF DESCRIPTION OF THE DRAWINGS

FIG. 1 shows the fluorescence pattern obtained on the Cytofluorograf after reacting normal human peripheral T cells with OKT3 at a 1:1000 dilution and G/M FITC. For comparison, results with monoclonal antibodies OKT1 and OKT4 are shown under equivalent conditions in FIGS. 1-5.

FIG. 2 shows the fluorescence pattern obtained on the Cytofluorograf after reacting human thymocytes with OKT3 and G/M FITC.

FIG. 3 shows the fluorescence pattern obtained on the Cytofluorograf after reacting leukemic cells from B cell chronic lymphoblastic leukemia patients with OKT3 and G/M FITC.

FIG. 4 shows the fluorescence pattern obtained on the Cytofluorograf after reacting the human T cell line HJD-1 with OKT3 and G/M FITC.

FIG. 5 shows the fluorescence pattern obtained on the Cytofluorograf after reacting the human T cell line CEM with OKT3 and G/M FITC.

The data in FIGS. 1-5 plus additional data for OKT3 (as well as OKT1 and OKT4) are summarized in Table I.

The production of the hybridoma and the production and characterization of the resulting monoclonal antibody were conducted as described in the above Examples. Although large quantities of the subject antibody were prepared by injecting the subject hybridoma intraperitoneally into mice and harvesting the malignant ascites, it is clearly contemplated that the hybridoma could be cultured in vitro by techniques well-known in the art and the antibody removed from the supernatant.

As shown in FIG. 1, the entire human peripheral blood T cell population of a given normal individual is reactive with OKT3, whereas the entire B cell, null cell, and macrophage populations isolated from the same individual are unreactive with OKT3. Similar results were obtained on populations of lymphocytes from fifteen other normal individuals. The monoclonal antibody is thus characterized in that it is reactive with an antigen contained on the surface of essentially all normal human peripheral T cells, while being unreactive with any antigens on the surface of the other three cell types discussed above. This differential reactivity is one test by which the subject antibody OKT3 may be detected and distinguished from other antibodies.

As shown in FIG. 2, the vast majority of normal human thymocytes from a six-month old infant are completely unreactive with OKT3, while about 5 to 10 percent of the thymocytes are reactive. The implication of this finding is that, during the differentiation process by which stem cells are converted into mature T cells, the thymocytes acquire at some stage the same surface antigen found on T cells, which is reactive with OKT3. It is believed that these thymocytes are in the later stages of differentiation just prior to emergence from the thymus into the bloodstream. Similar results (5-10% reactivity) were obtained using six additional thymus specimens from normal individuals two months to 19 years of age. The pattern of reactivity in FIG. 2 provides a second method of detecting the subject antibody OKT3 and distinguishing it from other antibodies.

The subject antibody is also useful for determining the proportion of circulating lymphocytes that are T cells. As shown in Table I, $\geq 95\%$ of all T cells react with OKT3 antibody. The present invention thus includes a method for determining in an individual the proportion of circulating lymphocytes that are T cells which comprises mixing OKT3 antibody with a lymphocyte composition from the individual and determining the preparation of the lymphocytes which are OKT3+, and thus T cells.

A further characterization of the subject antibody OKT3 is shown by the reactivity to various human T cell lines illustrated in FIGS. 4 and 5. As can be seen, the reactivity of the subject antigen to human T cell lines was heterogeneous, being weak for the line HJD-1, and nonexistent for the lines CEM, Laz 191, and HM1.

This differential reactivity of OKT3 to various readily-available human T cell lines provides yet another method of characterizing and describing the subject antibody. The lack of reaction of OKT3 with the human B cell lines Laz 007, Laz 156, Laz 256, and SB is shown in Table I. This further supports the lack of reactivity of OKT3 with B cells obtained from the peripheral blood of a normal human population and provides yet another method for characterizing and distinguishing the subject antibody OKT3.

The specific reaction of OKT3 antibody with an antigen on cutaneous T cell lymphomas is illustrated by Table II, where the distinction from OKT1 and OKT4 is shown. The present antibody thus provides a reagent for confirming a diagnosis of cutaneous T cell lymphoma in a patient suspected of having said disease. Treatment of cutaneous T cell lymphoma by administration of a therapeutically effective amount of OKT3 antibody is also contemplated as part of the present invention.

According to the present invention there are provided a hybridoma capable of producing antibody against an antigen found on essentially all normal human T cells and cutaneous T lymphoma cells, a method for producing this hybridoma, monoclonal antibody against an antigen found on essentially all human T cells, methods for producing the antibody, and methods for treatment or diagnosis of disease employing this antibody.

Although only a single hybridoma producing a single monoclonal antibody against human T cell antigen is described, it is contemplated that the present invention encompasses all monoclonal antibodies exhibiting the characteristics described herein. It was determined that the subject antibody OKT3 belongs to the subclass $IgG_2$, which is one of four subclasses of murine IgG. These subclasses of immune globulin G differ from one another in the so-called "fixed" regions, although an antibody to a specific antigen will have a so-called "variable" region which is functionally identical regardless of which subclass of immune globulin G it belongs to. That is, a monclonal antibody exhibiting the characteristic described herein may be of subclass $IgG_1$, $IgG_{2}a$, $IgG_{2}b$, or $IgG_3$, or of classes IgM, IgA, or other known Ig classes. The differences among these classes or subclasses will not affect the selectivity of the reaction pattern of the antibody, but may affect the further reaction of the antibody with other materials, such as (for example) complement or anti-mouse antibodies. Although the subject antibody is specifically $IgG_2$, it is contemplated that antibodies having the patterns of reactivity illustrated herein are included within the subject invention regardless of the immune globulin class or subclass to which they belong.

Further included within the subject invention are methods for preparing the monoclonal antibodies described above employing the hybridoma technique illustrated herein. Although only one example of a hybridoma is given herein, it is contemplated that one skilled in the art could follow the immunization, fusion, and selection methods provided herein and obtain other hybridomas capable of producing antibodies having the reactivity characteristics described herein. Since the individual hybridoma produced from a known mouse myeloma cell line and spleen cells from a known species of mouse cannot be further identified except by reference to the antibody produced by the hybridoma, it is contemplated that all hybridomas producing antibody having the reactivity characteristics described above are included within the subject invention, as are methods for making this antibody employing the hybridoma.

Further aspects of the invention are methods of treatment or diagnosis of disease employing the monoclonal antibody OKT3 or any other monoclonal antibody exhibiting the pattern of reactivity provided herein. As discussed above, the subject antibody allows treatment of patients having certain T cell chronic lymphoblastic leukemias by administration of a therapeutically-effective amount thereof. Administration of a therapeutically-effective amount of OKT3 antibody to an individual subject undergoing organ transplant will reduce or eliminate the rejection of this transplant. The subject antibody also allows detection of cutaneous T cell lymphoma in an individual by mixing a lymphoma T cell composition from said individual with a diagnostically-effective amount of OKT3 antibody. The presence of a reaction confirms the identity of the disease. The cutaneous T cell lymphoma may be treated by administering to an individual in need of such treatment a therapeutically-effective amount of OKT3 antibody. This antibody will react with and reduce the amount of T lymphoma cells, thus ameliorating the disease. In view of these diagnostic and therapeutic methods, the present invention additionally includes diagnostic and therapeutic compositions comprising (respectively) a diagnostically-effective or therapeutically-effective amount of OKT3 antibody in a diagnostically or pharmaceutically acceptable carrier.

TABLE I
MONOCLONAL ANTIBODY REACTIVITY AND PROPERTIES

| | Monoclonal Antibodies | | |
|---|---|---|---|
| | OKT1 | OKT3 | OKT4 |
| % Reactivity With: | | | |
| Peripheral T-cells (10 samples) | >95% | >95% | 55% |
| Peripheral B-cells (10 samples) | <2% | <2% | <2% |
| Peripheral Null cells (10 samples) | <2% | <2% | <2% |
| Thymocytes* (8 samples) | 5–10% | 5–10% | 80% |
| Reactivity With: | | | |
| T-chronic lymphatic Leukemia (3 cases) | + | +(1);−(2) | − |
| T-acute lymphatic Leukemia (8 cases) | − | − | − |
| Null acute lymphatic Leukemia (15 cases) | − | − | − |
| B-chronic lymphatic Leukemia (6 cases) | +(4);−(2) | − | − |
| B-cell lines+ (4) | − | − | − |
| T-cell lines+ HJD-1 | + | (±) | − |
| CEM | + | − | + |
| Laz 191 | + | − | − |
| HM1 | + | − | − |
| IgG Subclass | IgG$_1$ | IgG$_2$ | IgG$_2$ |
| Complement fixation | − | + | + |

*From patients aged 2 months to 18 years
+Obtained from Dr. H. Lazarus, Sidney Farber Cancer Center. B cell lines Laz 256, 156, 007 and SB obtained by Epstein-Barr virus transformation of human peripheral B cells and HJD-1, CEM, Laz 191, and HM1 established from leukemic patients.

TABLE II

| Patient's Name | Cutaneous T-Cell Lymphoma DIAGNOSIS | MONOCLONAL ANTIBODY ASSAYS | | |
|---|---|---|---|---|
| | | OKT1 | OKT3 | OKT4 |
| E. McBride | Sezary Blast Crisis; PBL | + | + | − |
| C. O. Okley | Mycosis Fungoides; Node | − | + | + |
| Odom | Mycosis Fungoides; Node | + | + | − |
| Montalbono | ? Node | + | + | + |

Source of cells: PBL = peripheral blood lymphocytes
Node = lymph node

What is claimed is:

1. A therapeutic composition of matter comprising, in admixture with a pharmaceutically-acceptable carrier, a therapeutically effective amount of a mouse monoclonal antibody, said amount being effective to reduce or eliminate the rejection of a transplant by an organ transplant recipient, said monoclonal antibody fixing complement and reacting with essentially all normal human peripheral T cells, but not with normal human peripheral B cells, null cells, or macrophages.

2. A therapeutic composition of matter comprising, in admixture with a pharmaceutically-acceptable carrier, a therapeutically effective amount of a mouse monoclonal antibody, said amount being effective to reduce or eliminate the rejection of a transplant by an organ transplant recipient, said monoclonal antibody fixing complement and reacting with essentially all normal human peripheral T cells.

3. A method of treatment of an organ transplant recipient to reduce or eliminate rejection of said transplanted organ which comprises administration to said recipient of an amount of mouse monoclonal antibody effective to cause said reduction or elimination, said antibody fixing complement and reacting with essentially all normal human peripheral T cells but not with normal human peripheral B cells, null cells, or macrophages.

4. A therapeutic composition of matter comprising, in admixture with a pharmaceutically acceptable carrier, a therapeutically-effective amount of monoclonal antibody produced from a hydriboma having the identifying characteristics of ATCC CRL 8001 said amount being effective to reduce or eliminate the rejection of a transplant by an organ transplant recipient.

5. A therapeutic composition of matter comprising, in admixture with a pharmaceutically acceptable carrier, a therapeutically-effective amount of monoclonal antibody, said amount being effective to reduce or eliminate the rejection of a transplant by an organ transplant recipient, which antibody:
  (a) reacts with essentially all normal human peripheral T cells and cutaneous T lymphoma cells, but not with normal human peripheral B cells, null cells or macrophages;
  (b) reacts with from about 5% to about 10% of normal human thymocytes;
  (c) reacts with leukemic cells from humans with T cell chronic lymphoblastic leukemia but does not react with leukemic cells from humans with T cell acute lymphoblastic leukemia, null cell acute lymphoblastic leukemia, or B cell chronic lumphatic leukemia;
  (d) reacts weakly with the human T cell line HJD-1 but does not react with CEM, Laz 191, or HM1;
  (e) does not react with the Epstein-Barr virus-transformed human B cell lines Laz 007, Laz 156, Laz 256, or SB; and (f) fixed complement.

6. A method of treatment of an organ transplant recipient to reduce or eliminate rejection of said transplanted organ which comprises administration to said recipient of an amount of mouse monoclonal antibody effective to cause said reduction or elimination, said antibody fixing complement and reacting with essentially all normal human peripheral T cells.

7. A method of treatment of an organ transplant recipient to reduce or eliminate allograft rejection of said transplanted organ which comprises administration of an amount of monoclonal antibody effective to cause said reduction or elimination, which antibody:
(a) reacts with essentially all normal human peripheral T cells and cutaneous T lymphoma cells, but not with normal human peripheral B cells, null cells or macrophages;
(b) reacts with from about 5% to about 10% of normal human thymocytes;
(c) reacts with leukemic cells from humans with T cell chronic lymphoblastic leukemia but does not react with leukemic cells from humans with T cell acute lymphoblastic leukemia, null cell acute lymphoblastic leukemia, or B cell chronic lymphatic leukemia;
(d) reacts weakly with the human T cell line HJD-1 but does not react with CEM, Laz 191, or HM1;
(e) does not react with the Epstein-Barr virus-transformed human B cell lines Laz 007, Laz 156, Laz 256, or SB; and
(f) fixes complement.

8. The method of claim 7 wherein the antibody is produced from a hybridoma having the identifying characteristics of ATCC CRL 8001.

9. A diagnostic composition for determining in an individual the proportion of circulating lymphocytes that are T cells which comprises a diagnostically-effective amount of a mouse monoclonal antibody that fixed complement and reacts with essentially all normal human peripheral T cells, but not with normal human peripheral B cells, null cells, or macrophages, said antibody being admixed with a diagnostically acceptable carrier.

10. A diagnostic composition for determining in an individual the proportion of circulating lymphocytes that are T cells which comprises a diagnostically-effective amount of a mouse monoclonal antibody that fixed complement and reacts with essentially all normal human peripheral T cells, said antibody being admixed with a diagnostically acceptable carrier.

11. A diagnostic composition for determining in an individual the proportion of circulating lymphocytes that are T cells which comprises a diagnostically-effective amount of a mouse monoclonal antibody that reacts with essentially all normal human peripheral T cells, but not with normal human peripheral B cells, null cells, or macrophages, said antibody being admixed with a diagnostically acceptable carrier.

12. A diagnostic composition for determining in an individual the proportion of circulating lymphocytes that are T cells which comprises a diagnostically-effective amount of a mouse monoclonal antibody that reacts with essentially all normal human peripheral T cells, said antibody being admixed with a diagnostically acceptable carrier.

13. A diagnostic composition for determining in an individual the proportion of circulating lymphocytes that are T cells which comprises a diagnostically-effective amount of a mouse monoclonal antibody having the identifying characteristics of that produced by hybridoma ATCC CRL 8001, said antibody being in admixture with a diagnostically acceptable carrier.

14. A method for determining in an individual the proportion of circulating lymphocytes that are T cells which comprises mixing an effective determining amount of a monoclonal antibody with a circulating lymphocyte composition from said individual and determining the proportion of the circulating lymphocytes which react with said antibody, and are thus T cells, which antibody:
(a) reacts with essentially all normal human peripheral T cells and cutaneous T lymphoma cells, but not with normal human peripheral B cells, null cells or macrophages;
(b) reacts with from about 5% to about 10% of normal human thymocytes;
(c) reacts with leukemic cells from humans with T cell chronic lymphoblastic leukemic but does not react with leukemic cells from humans with T cell acute lymphoblastic leukemia, null cell acute lymphoblastic leukemia, or B cell chronic lymphatic leukemia;
(d) reacts weakly with the human T cell line HJD-1 but does not react with CEM, Laz 191, or HM1;
(e) does not react with the Epstein-Barr virus-transformed human B cell lines Laz 007, Laz 156, Laz 256, or SB; and
(f) fixed complement.

15. A method for determining in an individual the proportion of circulating lymphocytes that are T cells which comprises mixing an effective determining amount of antibody produced from a hybridoma having the identifying characteristics of OKT3 with a circulating lymphocyte composition from said individual and determining the proportion of the circulating lymphocytes which react with said antibody, and are thus T cells.

* * * * *